US008905926B2

(12) United States Patent
Colombo et al.

(10) Patent No.: US 8,905,926 B2
(45) Date of Patent: Dec. 9, 2014

(54) REHABILITATION SYSTEM FOR NEUROLOGICAL DISORDERS

(75) Inventors: Gery Colombo, Uster (CH); Reinhard Schreier, Winterthur (CH); Robert Riener, Wangen (CH); Martin Wieser, Zurich (CH); Jonas Fisler, Wettingen (CH)

(73) Assignee: Hocoma AG, Volketswil (CH)

( * ) Notice: Subject to any disclaimer, the term of this patent is extended or adjusted under 35 U.S.C. 154(b) by 1009 days.

(21) Appl. No.: 12/209,649

(22) Filed: Sep. 12, 2008

(65) Prior Publication Data
US 2009/0076351 A1 Mar. 19, 2009

(30) Foreign Application Priority Data

Sep. 13, 2007 (EP) ..................................... 07116315

(51) Int. Cl.
*A61B 5/0482* (2006.01)
*A61H 1/00* (2006.01)
*A61B 5/00* (2006.01)

(52) U.S. Cl.
CPC .............. *A61H 1/00* (2013.01); *A61H 2230/08* (2013.01); *A61B 5/486* (2013.01); *A61B 5/0482* (2013.01)
USPC .......................................... 600/301; 600/300

(58) Field of Classification Search
None
See application file for complete search history.

(56) References Cited

U.S. PATENT DOCUMENTS

| 4,883,067 | A  | * | 11/1989 | Knispel et al. | ................ | 600/545 |
| 4,926,969 | A  | * | 5/1990  | Wright et al.  | ................ | 600/544 |
| 6,547,746 | B1 | * | 4/2003  | Marino         | ......................... | 600/554 |
| 7,460,903 | B2 | * | 12/2008 | Pineda et al.  | ................ | 600/544 |
| 8,095,209 | B2 | * | 1/2012  | Flaherty       | ...................... | 600/544 |
| 8,753,296 | B2 | * | 6/2014  | Einav et al.   | ...................... | 601/5  |
| 2006/0149338 | A1 | * | 7/2006 | Flaherty et al. | ................ | 607/49 |
| 2007/0032738 | A1 | * | 2/2007 | Flaherty et al. | ................ | 600/545 |
| 2007/0287931 | A1 | * | 12/2007 | Dilorenzo     | ..................... | 600/545 |
| 2007/0293732 | A1 | * | 12/2007 | Delahunt et al. | ............. | 600/300 |

FOREIGN PATENT DOCUMENTS

| AU | 636287 B2    | 4/1993  |
| WO | 0136051 A2   | 5/2001  |
| WO | 2005105203 A1 | 11/2005 |
| WO | 2006021952 A2 | 3/2006  |
| WO | 2006074029 A2 | 7/2006  |

\* cited by examiner

*Primary Examiner* — William Thomson
*Assistant Examiner* — Bobby Soriano
(74) *Attorney, Agent, or Firm* — The Webb Law Firm

(57) ABSTRACT

A rehabilitation system for neurological disorders, especially for the rehabilitation of patients being in a vegetative state or minimal conscious state, comprises at least two sensors adapted to measure two different physiological values of the patient and a stimulation generator. Initially predefined target signals determined and based on parameters relating to the injury are generated and, during a rehabilitation session, compared with the measurement signals to drive the stimulation generators delivering sensory stimulation to the patient as feedback. The controlling processor is adapted to change the predefined target signals during a rehabilitation session based on the development or changes of the measurement signals of the different physiological values, to enable a faster and better improvement of the alertness of the patient.

11 Claims, 6 Drawing Sheets

REHABILITATION SYSTEM FOR NEUROLOGICAL DISORDERS

FIELD OF THE INVENTION

The invention relates to a rehabilitation system for neurological disorders, especially a system for the rehabilitation of patients being in a vegetative state or minimal conscious state.

BACKGROUND OF THE INVENTION

WO 01/36051 describes a motor learning system for rehabilitation of neurological disorders and especially to orthopedic limb injuries. Said device comprises an insole or pad including a pressure sensor and/or force sensor to measure the weight force applied to at least two monitored locations of at least one limb of a patient. The sensors are connected to a computer processor making a comparison of the determined weight values against a predefined target weight distribution. Said target weight distribution is based on parameters unique to the patient and the injury. The processor is adapted to drive a stimulator delivering closed-loop sensory stimulation as feedback to encourage the patient to distribute said weight more evenly. The sensory stimulation can comprise visual and/or audio effects as well as mechanical vibrations.

Such a device is adapted to be used by a patient being able to actively follow the program defined through application of said target parameters and which patient decides about his actions. The aim of the device is to help a patient to find the equal weight distribution. Based on static inputs as e.g. gender and biomechanical properties of the fixation of the injury and quasi-static inputs as e.g. time post-injury and weight a initial rehabilitation program is generated, including e.g. bandwidth range and frequency of the walking patient. During the session the patient receives said feedback information to improve his performance. After completing a session the data set of acquired information is compared to the predefined success criteria and the initial rehabilitation program is adapted to better suit the needs of the patient for a following session.

Said system is not suitable for patients in a vegetative state or minimal conscious state.

Furthermore the known device initially generates predefined target signals determined and based on input parameters and then delivers—during a rehabilitation session—sensory stimulation to the patient as feedback based on a comparison of the measurement signals with target signals. Only after one completed rehabilitation session the predefined target signals for a subsequent rehabilitation session are adapted following the result of the completed rehabilitation session.

SUMMARY OF THE INVENTION

It is therefore an object of the present invention to provide a rehabilitation system for neurological disorders, especially for patients being in a vegetative state or minimal conscious state.

It is a further object of the invention to provide a rehabilitation system allowing an improvement of the alertness and awareness of such patients.

Furthermore, it is an object of the invention to provide a system detecting and quantifying the state of alertness to optimize the awakening process in such vegetative and minimal conscious patients.

The invention is based on the insight that the adoption of the sensory answer of the system has preferably to be adapted during a session.

Furthermore the invention uses preferably at least two different physiological parameters and two different physiological signals retrieved by sensors to control the output of preferably at least two different displays.

Furthermore it has been found that physiological reactions of patients being in a vegetative state or minimal conscious state are distributed in different time frames; the awakening process can be optimized taking into account different closed-loop controllers.

It is advantageous that during a rehabilitation session, the system can hop to a different 'initial' parameter set. For this a time interval is defined and the change of the initial measurement signals to the current measurement signals is compared to said improvement threshold value or vector. If the improvement does not reach a predefined threshold value or vector the one or more of the stimulation generators delivering sensory stimulation to the patient as feedback are reset to follow new predefined target signals.

SHORT DESCRIPTION OF THE DRAWINGS

The invention is now described with reference to the enclosed drawings.

DETAILED DESCRIPTION OF PREFERRED EMBODIMENTS

FIG. 1 to 8 show rehabilitation devices encompassing—inter alia—different controller strategies. Similar features in all embodiments receive the same reference signs and are usually only described in detail in the first described embodiment in which they appear.

Figure 1:
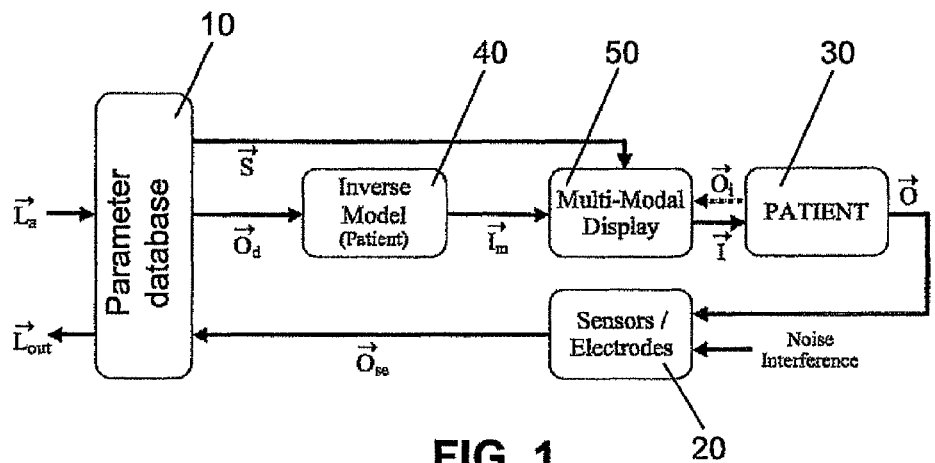
FIG. 1 shows a rehabilitation device according to a first embodiment of the invention using an open-loop/feedforward control.

FIG. 1 shows a rehabilitation device according to a first embodiment of the invention using an open-loop/feedforward control.

The rehabilitation device comprises a interpreter computer unit 10 named parameter database in FIG. 1. This unit 10 comprises input and output facilities. The arrow $\vec{L}_a$ relates to a vector called 'level of alertness' which is to be defined as a set of parameters. The same set of parameters describes the 'actual level of alertness' $\vec{L}_{out}$, i.e. comprising the same vector elements. These elements are physiological quantities. Such physiological quantities can be chosen from the group encompassing e.g. EEG signals and Evoked Potentials, EMG signals, heart rate, systolic and diastolic blood pressure, respiration frequency, skin conductance, oxygen saturation, body temperature, etc.

These physiological quantities are measurement signals which can be acquired through sensors 20, which are applied to a patient 30. Additionally, of course, the sensors 20 also receive noise and interference signals, which preferably are filtered at least in the computer 10. The signals $\vec{O}_{se}$ will be acquired by means of sensors and electrodes 20 to measure non-electrical and bioelectrical physiological signals, respectively.

The database of parameters of computer 10 can also be called to be an interpreter, since this database is filled and identified on the basis of objective parameters retrieved through experimental investigations, and subjective fixation of alertness conditions based on literature reviews and knowledge of experienced medical doctors. Hence, the reference vector with predicted values $\vec{O}_d$ will be the input to an inverse dynamic model 40 describing the physiological processes of the patient. The model 40 determines the required input signals $\vec{T}_m$ fed to the display devices 50 (feedforward loop). Moreover the interpreter computer 10 sends signals $\vec{S}$ to drive display modes and switch on/off display devices. The control can be described as an array to image the input vector onto a selected output vector.

Models 40 are known from the prior art, e.g. Timischl, S. "A Global Model for the Cardiovascular and Respiratory System" published as PhD thesis, Karl-Franzens University of Graz, August 1998. Another model is focused on the analysis of slow dynamical variations of long term neurophysiological parameters like the partial oxygen pressure of brain tissue or the cerebral blood flow, disclosed by Jung et al. "A mathematical model of cerebral circulation and oxygen supply".

Some solutions for different display devices 50 are shown in the following table.

| Display device | Example |
| --- | --- |
| leg or arm movement generator | a stepper like disclosed in WO00/61059 |
| tilting board/bench for body verticalisation | a tilting table like disclosed in WO00/61059 |
| graphical display | a monitor |
| acoustic display | loud speakers, headphones |
| tactile stimulator | a vibrator unit |
| olfactory display | Via odour vaporization |
| heat or cold display | IR lamp for heating or peltier element for cooling |

The patient will show a physiological output $\vec{O}$ on the display 50 and can react with an interaction $\vec{O}_i$ to the display 50. Such an interaction can be a reflex or a change of a subconscious physiological condition. Such a change can occur fast (in seconds) as in case of the heart rate or slowly (in minutes) as in case of some EEG patterns.

It is advantageous that during a rehabilitation session, the system can hop to a different 'initial' parameter set, i.e. to apply different stimulation values or simply different stimulation, i.e. it is possible to initially use an acoustic display and after several minutes the acoustic display is changed or replaced by or added to a graphical display. For this a time interval is defined and the change of the initial measurement signals to the current measurement signals is compared to said improvement threshold value or vector. If the improvement does not reach a predefined threshold value or vector within the responses, e.g. eye movement, heart rate change etc., the one or more of the stimulation generators delivering sensory stimulation to the patient as feedback are reset to follow new predefined target signals. Usually the same already applied sensors 20 are continuously acquiring the same measurement signals.

Figure 2:
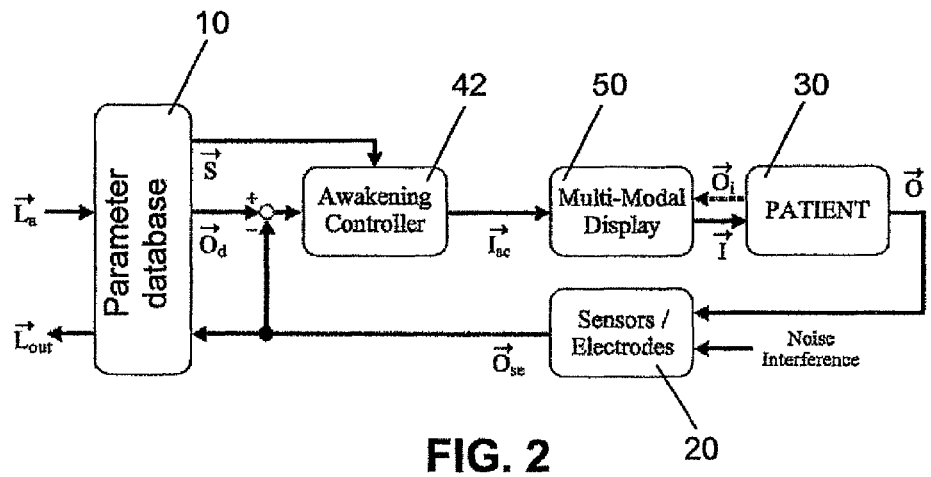
FIG. 2 shows a rehabilitation device according to a second embodiment of the invention using a feedback control.

FIG. 2 shows a rehabilitation device according to a second embodiment of the invention using a feedback control. The system uses identical units 10, 20, 30, 40 and 50. The inverse model of the patient of FIG. 1 is adapted to become the so called awakening controller 42. In the feedback loop recorded signals $\vec{O}_{se}$ will be compared to the reference values $\vec{O}_d$ and the error fed into the (awakening) controller 42. The controller 42 then determines the required input signals $\vec{T}_{ac}$ inducted to the display devices 50.

Figure 3:
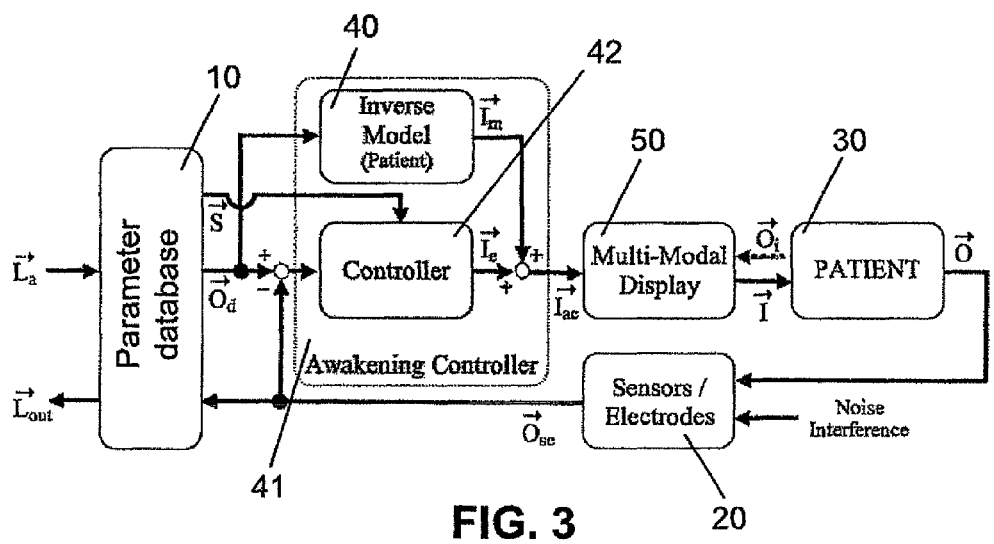
FIG. 3 shows a rehabilitation device according to a third embodiment of the invention using a combination of feedforward and feedback control.

FIG. 3 shows a rehabilitation device according to a third embodiment of the invention using a combination of feedforward and feedback control. Therefore the awakening controller unit 41 comprises beside the inverse model 40 the controller 42 from FIG. 2. The predicted error vector $\vec{T}_e$ is calculated by controller 42 which receives the input signals as in FIG. 2.

Additional to the separated control strategies as mentioned in connection with FIG. 1 and FIG. 2 the predicted error vector $\vec{T}_e$ and the output $\vec{T}_m$ of the inverse human model 41 will sum up and define the input $\vec{T}_{ac}$ to the multi-modal display 50. The display 50 will expose the patient to the defined sensory modalities $\vec{T}$.

Figure 4:
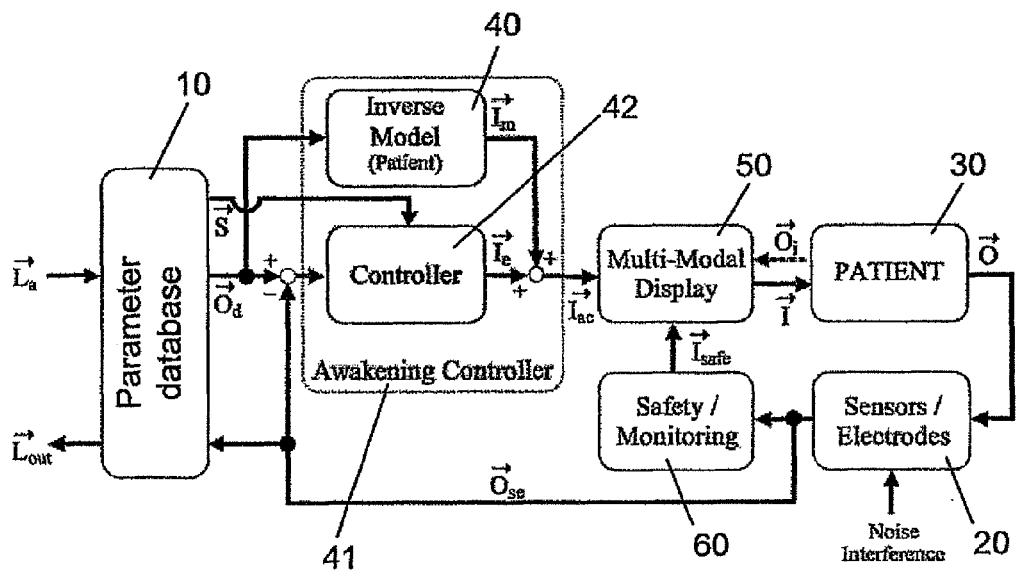
FIG. 4 shows a rehabilitation device according to a fourth embodiment of the invention using the combined control strategy according to FIG. 3 with safety extension.

FIG. 4 shows a rehabilitation device according to a fourth embodiment of the invention using the combined control strategy according to FIG. 3 with safety extension.

The physiological values retrieved by the sensors 20 will be checked via a monitoring device 60. Defined thresholds will influence the actuation and drive of the display 50 (e.g. movement generator, tilting board, acoustic display) in a safe mode. E.g. after detecting a heart rate as physiological value detected by one of the sensors 20 being over the threshold value, the inclination angle sa of a tilting board will decrease for some degrees or back to zero.

Figure 5:
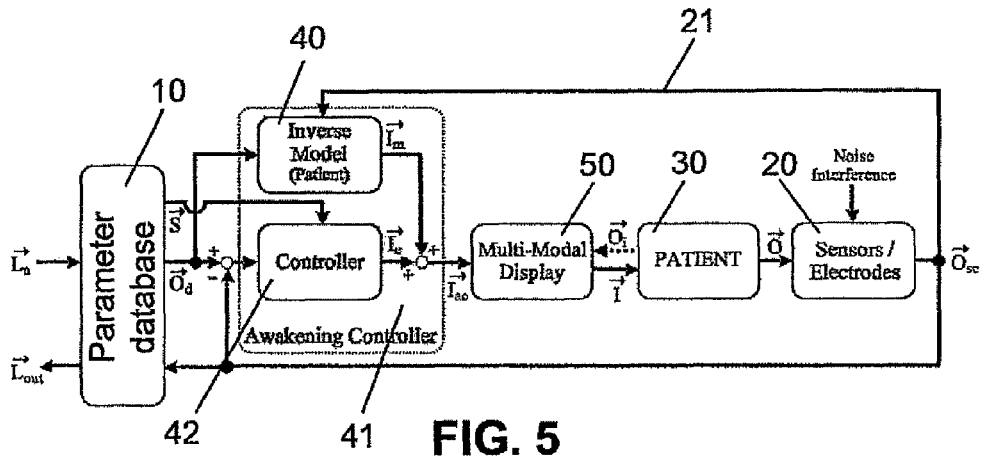
FIG. 5 shows a rehabilitation device according to a fifth embodiment of the invention using the combined control strategy according to FIG. 3 with additional input for the model.

FIG. 5 shows a rehabilitation device according to a fifth embodiment of the invention using the combined control strategy according to FIG. 3 with additional input 21 for the model 40. Additional to the controller 42 the inverse dynamic model 40 will get a feedback of the real measured physiological values through line 21. The information will be used to adjust individually to the situation of the treated patient.

Although FIG. 5 does not show a safety extension unit 60, it is clear that the different descriptions of different embodiments in connection with FIG. 1 to 8 and their application and actual use in connection with FIG. 9 to 15 does not mean, that they have to be seen isolated one-by-one, but that the invention also comprises the combination of the features shown, i.e. someone skilled in the art will apply a safety extension 60 as disclosed in connection with FIG. 4 to a device according to one of FIG. 1, 2 or 5 and subsequent Figure as well as the additional feedback line 21 can also be incorporated in various embodiments, as for example in embodiments according to FIG. 1, 3 or 4.

Figure 6:
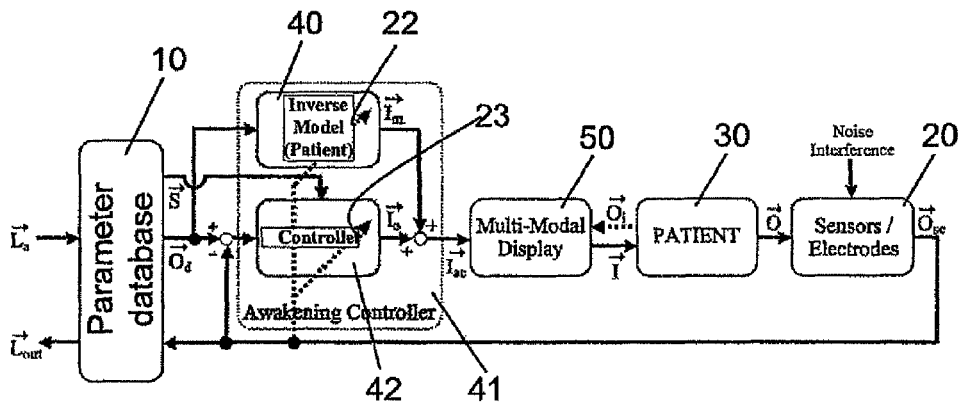
FIG. 6 shows a rehabilitation device according to a sixth embodiment of the invention using the combined control strategy according to FIG. 3 with additional adaptive extension input for the model and the controller.

FIG. 6 shows a rehabilitation device according to a sixth embodiment of the invention using the combined control strategy according to FIG. 3 with additional adaptive extension input 22 for the model 40 and the controller 41.

The main difference to the previous control strategies is the adaptive part 22, 23. By means of the recorded signals $\vec{O}_{se}$ the two parts of the awakening controller 41, i.e. the inverse model 40 and controller 42 will be adapted during the training with signal paths 22 and 23, respectively. This relates to a direct sensor input into the inverse model 40 and the controller 42 additionally to the feedback with inclusion of parameters based on and stored in the parameter database unit 10.

Figure 7:
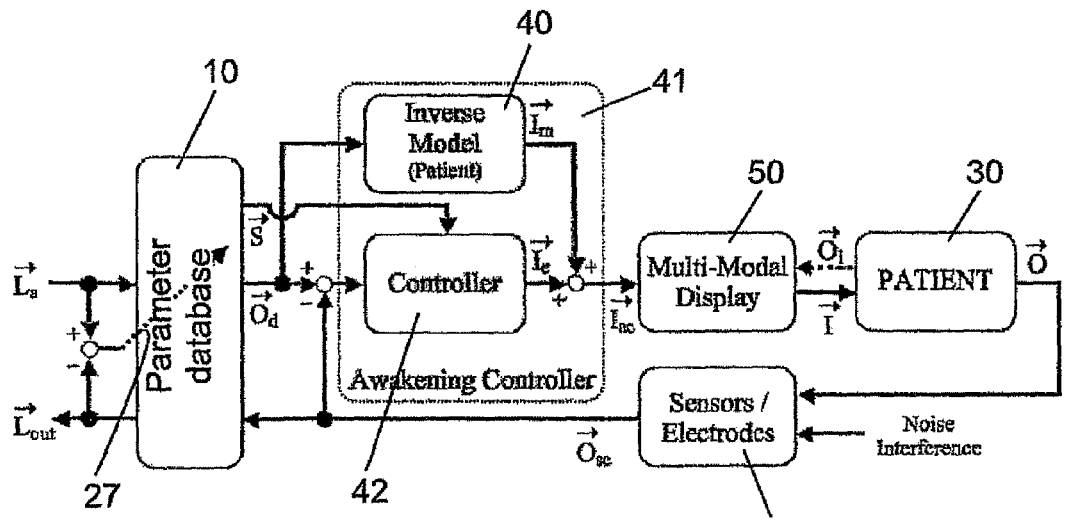
FIG. 7 shows a rehabilitation device according to a seventh embodiment of the invention using the combined control strategy according to FIG. 3 with additional adaptive extension input for the interpreter computer unit.

FIG. 7 shows a rehabilitation device according to a seventh embodiment of the invention using the combined control strategy according to FIG. 3 with additional adaptive extension input 24 for the interpreter computer unit 10. Here the adjustment will be driven by the error between the defined level of alertness $\vec{L}_a$ and the actual level of alertness $\vec{L}_{out}$.

Figure 8:
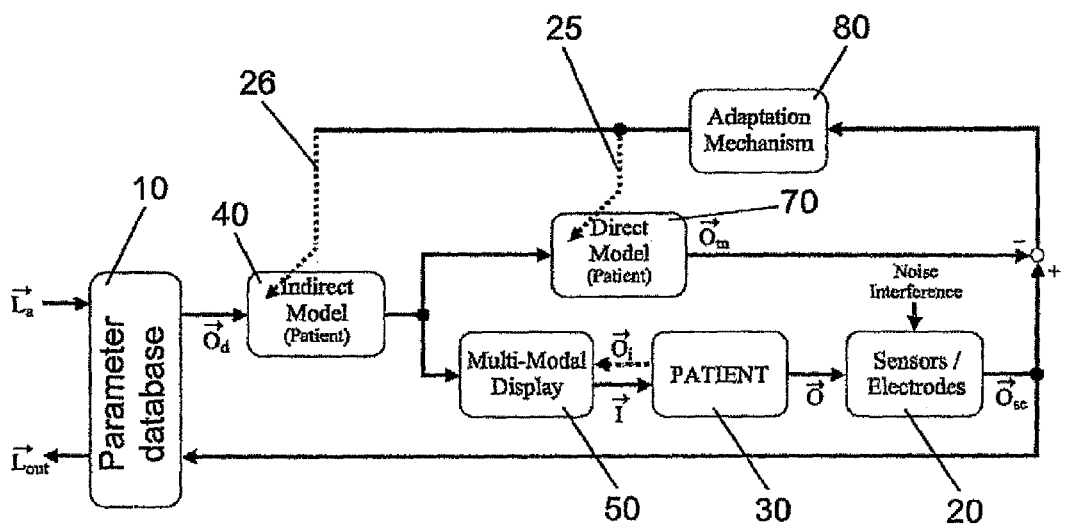
FIG. 8 shows a rehabilitation device according to a eighth embodiment of the invention using the control strategy according to FIG. 1 using a direct model with additional adaptive input.

FIG. 8 shows a rehabilitation device according to a eighth embodiment of the invention using the control strategy according to FIG. 1 using a direct model 70 with additional adaptive input paths 25 and 26 for the direct model 70 and the indirect model 40, respectively. In the model adaptive control strategy the inverse dynamic model 40 delivers the predicted input values for the multi-modal display 50 and the direct dynamic model 70 of the patient 30. The direct and the inverse dynamic model are identical except that they are 'reversed' with respect to each other. In this approach, the direct dynamic model is an 'observer' of the reaction to the exposed stimuli. The error between the physiological output signals $\vec{O}_m$ predicted by the direct dynamic model and the recorded outcome $\vec{O}_{se}$ will drive the adaptation mechanism 80 issuing the signals on the paths 25 and 26. In this respect the direct feedback come in addition to the input of the database 10 in a way similar to the embodiment according to FIG. 6.

Someone skilled in the art will note that different solutions can be chosen to build the controllers 10, 42 as well as controllers 40 and 70. Some examples will now be disclosed to illustrate the possibilities without limiting the scope of the invention. The examples are:
(1) P, PI, PD or PID controller
(2) Direct Pole Placement
(3) Model Predictive Controller
(4) Adaptive controller
(5) Intelligent controller
(6) Non-Linear Control Systems A proportional-integral-derivative controller (PID controller) attempts to correct the error between measured process variables $\vec{O}_{se}$ and desired setpoints $\vec{O}_d$. By calculating and then outputting a corrective action the process can be adjusted accordingly, based upon three parameters (proportional, integral and derivative values). If $\vec{I}_e(t)$ is the control signal sent to the display and $\vec{O}_{err}(t)=\vec{O}_{se}(t)-\vec{O}_d(t)$, a PID controller has the general form $$\vec{I}_e(t) = \vec{K}_P \vec{O}_{err}(t) + \vec{K}_I \int \vec{O}_{err}(t)dt + \vec{K}_D \frac{d\vec{O}_{err}(t)}{dt}$$

$K_P$, $K_I$ and $K_D$ are vectors for the proportional, integral and derivative term, respectively. Stability can often be ensured using only the proportional term. The integral term permits the rejection of a step disturbance and the derivative term is used to provide damping or shaping of the response.

Here one can also think about only using one or two modes to provide the appropriate system control. The controller will be called a PI, PD, P or I controller in absence of respective control actions.

Direct pole placement can be performed mathematically using a state space representation of the open-loop system and calculating a feedback matrix assigning poles in the desired positions, in view of the fact that the system to handle is a multi-input multi-output (MIMO) system.

Model predictive controllers (MPC) rely on dynamic models of the process, most often linear empirical models obtained by system identification. The models are used to predict the behaviour of the dependent variables $\vec{I}_e(t)$ of a dynamical system with respect to changes in the process independent vectors $\vec{O}_{se}$ and $\vec{O}_d$.

The model predictive controller uses the models and current plant measurements to calculate future moves in the independent variables that will result in operation that honours all independent and dependent variables constraints.

The MPC is a multivariable control algorithm that uses (1) an internal dynamic model of the process, (2) a history of past control moves (3) an optimization cost function over the prediction horizon, to calculate the optimum control moves. One example for the cost function can be to minimize the absolute value of the error $\vec{O}_{err}$.

Adaptive control uses on-line identification of the process parameters, or modification of controller gains, thereby obtaining strong robustness properties.

Using this approach in combination with a PID controller, the values for $\vec{K}_P$, $\vec{K}_I$ and $\vec{K}_D$ will be updated by the identification. The structure of the controller itself will keep the same.

Intelligent control uses various computing approaches like Fuzzy Logic, Bayesian probability, support vector machines or artificial neural networks to control the dynamic system.

A fuzzy control system is a control system based on Fuzzy Logic—a mathematical system that analyzes analogue input values (often rough or "fuzzy" qualitative information) in terms of logical variables that take on continuous values between 0 and 1. As an example you can think about the change of the heart rate. The heart rate can be static, slightly increased or decreased, medium increased or decreased and so on. All the input variables in a fuzzy control system are in general mapped into by sets of membership functions, also known as 'fuzzy sets', the basic requirement for the controller.

Support vector machines (SVMs) are a set of related supervised learning methods used for classification and regression. They belong to a family of generalized linear classifiers. A special property of SVMs is that they simultaneously minimize the empirical classification error and maximize the geometric margin; hence they are also known as maximum margin classifiers. The input vectors are $\vec{O}_{se}(t)$ and $\vec{O}_A(t)$ but also derivations, integrations or correlations between single signals like galvanic skin response and body temperature or heart rate and oxygen saturation. All vectors that belong to the same state of alertness built a set of data points. Support vector machines map all input vectors (different sets of data points) to a higher dimensional space where a maximal separating hyperplane is constructed. So the nearest distance between a point in one separated hyperplane and a point in the other separated hyperplane is maximized and this is the basic idea of the controller. SVMs are well known in recognition of speech, objects and gesture—here they are used to recognize the state of alertness.

An artificial neural network (ANN) is an interconnected group of artificial neurons that uses a mathematical model or computational model for information processing based on a connectionist approach to computation. ANN is an adaptive system that changes its structure based on external or internal information that flows through the network. The input vectors are again $\vec{O}_{se}(t)$ and $\vec{O}_A(t)$ and derived signals. The output vector of the controller is $\vec{T}_e(t)$. The word 'network' in the term 'artificial neural network' arises because the function $f(x)$ is defined as a composition of other functions $g_i(x)$, which can further be defined as a composition of other functions. This can conveniently represented as a network structure, with arrows depicting the dependencies between variables. For example the heart rate is a function of blood pressure and the galvanic skin response signal.

But the blood pressure itself is also a function of the galvanic skin response signal, the resistance of the vessels and the respiration frequency. This is only the beginning of the whole network and a widely used type of composition is the nonlinear weighted sum. A lot of experimental data is required to train and validate the ANN controller: a subset of data will be used to train (teach) an 'empty' ANN and adapt its characteristics to optimally control the plant (patient) via the parameters of $\vec{T}_e(t)$. Another subset of data is used to validate (test) the controller.

Vegetative and minimal conscious state patients can show a behaviour with strong non-linear dynamics. In control theory it is sometimes possible to linearize such classes of systems and apply linear techniques: in our case with patients it is possible to devise control strategies of non-linear systems, especially the 'intelligent control strategies' can be combined with non-linear parts.

In general the models (indirect model, inverse model or direct model) are based on mathematical principles like artificial neural network, Fuzzy Logic or numerical approaches. Dynamic models are required as components within the control strategies in order to predict, observe, interpret, or control the behaviour of the plant (patient).

Kappel F. and Peer, R. O. proposed "A mathematical model for fundamental regulation processes in the cardiovascular system" in Journal of Mathematical Biology, 6:611-631, 1993. The article presented a mathematical model for the fundamental processes of the cardiovascular system. Further work on modelling was reported by Timischl (see above), who included also a respiratory model. Both models use a closed-loop feedback system regulating the cardiovascular system with optimal control theory.

As an example, based on this model an extension was derived to describe some specific cardiovascular relationships while using a stepper like disclosed in a device as disclosed WO00/61059. The inclination angle sa and the stepping frequencies $s_{ste}$ for performing the stepping patterns was chosen as an input of the model. The output includes heart rate ($f_{HR}$) and mean blood pressure ($p_m$). A non-linear model with linear, exponential and sigmoid-functions as well as $2^{nd}$ order differential equations was used. The identification of the model was done with a least-square algorithm. The output of the model as well as the measured output of a healthy person is shown in FIGS. 9 and 10.

Figure 9:
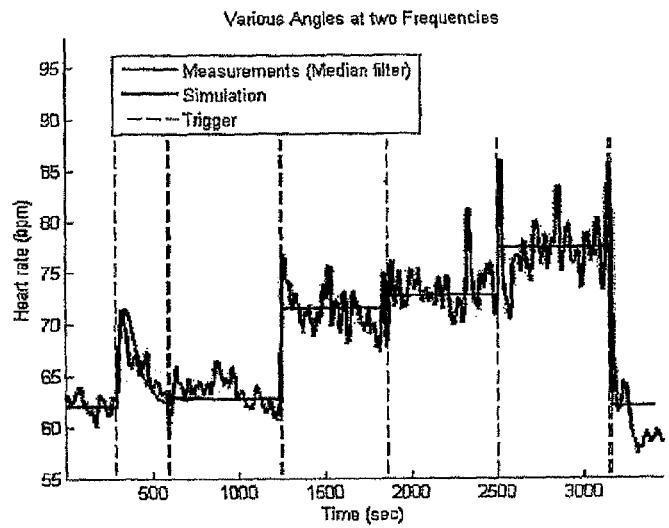
FIG. 9 shows the heart rate as sensor input over time at various angles as display of a system according to the invention at two frequencies.

FIG. 9 shows the heart rate over time at various angles at two frequencies using a system according to an embodiment of the invention as seen in FIG. 3 or 4. The output value is the heart rate; the triggers are ongoing in time: Trigger 1: Start leg drives 0.4 Hz, Trigger 2: Tilt to 20°, Trigger 3: Tilt to 55°, Trigger 4: Tilt to 75°, Trigger 5: Stop leg movement, Trigger 6: Tilt to 0°.

Figure 10:
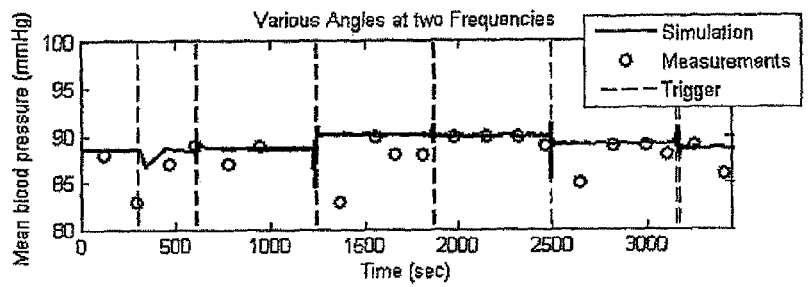
FIG. 10 shows the mean blood pressure as sensor input over time at various angles as display of a system according to the invention at two frequencies.

FIG. 10 shows the mean blood pressure over time at various angles at two frequencies using a system according to an embodiment of the invention as seen in FIG. 3 or 4. The output value is the blood pressure; the triggers are ongoing in time: Trigger 1: Start leg drives 0.4 Hz, Trigger 2: Tilt to 20°, Trigger 3: Tilt to 55°, Trigger 4: Tilt to 75°, Trigger 5: Stop leg movement, Trigger 6: Tilt to 0°.

After initial 5 minutes (300 seconds) laying in supine position, the stepping drives are switched on ($s_{ste}$=0.4 Hz). A clear increase of around 9 bpm can be seen that decreases back to the baseline within the next couple of minutes. This cardiac response has been modelled because of the reflexes that are triggered through passive leg movement. At t=600 s, the inclination angle $s_\alpha$ changes from 0° to 20°. The heart rate increases slightly. The large change in heart rate happens at the tilt from 20° to 55° (t=1230 s). The change to 75° again induces just a slight increase in heart rate (t=1860 s). Both of these reactions coincide with the model. At t=2490 s, when the leg drives are turned off, a clear increase in heart rate is detectable. This is included in the model because the passive leg movement supports the venous return. When stopping the leg movement this support ends and the heart must maintain a sufficient blood circulation. After returning to 0° tilting angle, the cardiac rate drops.

Inspecting the blood pressure measurements, it can be seen that blood pressure stays almost constant. At the positions, where a large change in heart rate occurs (t=300 s, 1230 s, 2490 s) no significant change in blood pressure can be seen. The parameters for peripheral resistance of the blood vessels of the model have been identified to have an almost constant blood pressure during the experiment. Because the heart rate increases, the peripheral resistance must decrease, otherwise the blood pressure would rise.

Figure 11:
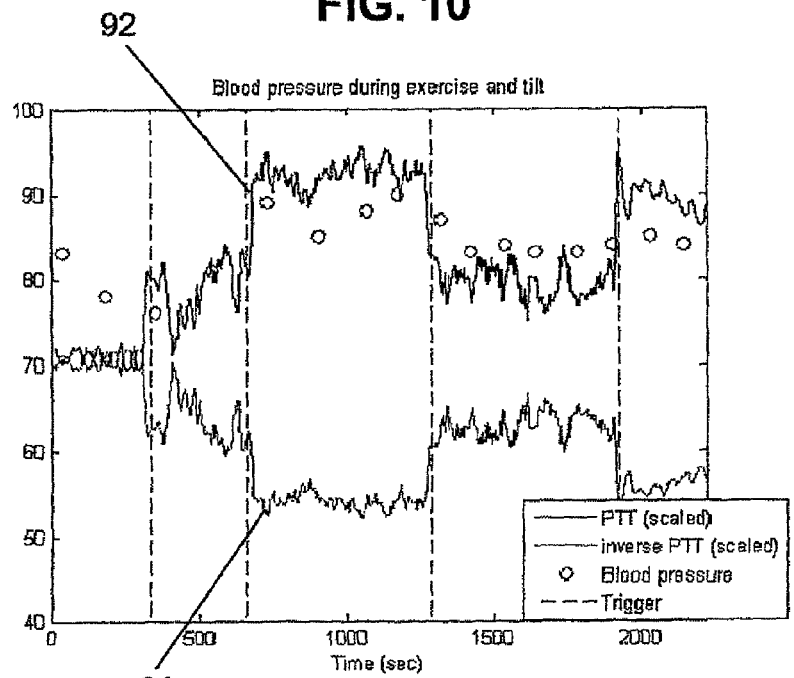
FIG. 11 shows pulse transit time (PTT) scaled and the inverted PTT values as sensor input.

FIG. 11 shows pulse transit time (PTT) 91 and the inverted PTT values 92, blood pressure in [mmHg] and relative gradient of the PTT values for the same environment as explained in connection with FIGS. 9 and 10; Trigger 1: Start of 0.8 Hz active stepping, Trigger 2: Tilt to 75°, Trigger 3: Stop movement, Trigger 4: Tilt to 0°.

An alternative blood pressure determination is the time between the heart contraction (recorded with the ECG) and the arrival of the pulse wave at the extremity (detected with a piezo pulse sensor), the pulse transit time (PTT). The PTT is the time of the pulse wave propagating between two different sites in the arterial system. It is known from the art that the speed of the pulse wave is directly proportional to the blood pressure. Hence, if the blood pressure rises the arterial walls become stiffer and PTT decreases, and conversely, when blood pressure falls, vascular tone decreases and PTT increases. Therefore FIG. 11 shows the pulse transit times 91 and the inverted pulse transit times 92, being mirrored at approximately 70 mm HG.

In FIG. 11 a clear change in blood pressure can be seen. PTT decreases as the subject starts to move the legs actively. In upright posture and still in active movement, PTT stays constant and rises to a higher constant level when stopping the leg activity. After the return to 0° PTT decreases again.

This example of a model with 2 inputs and 2 outputs shows that it is possible to predict the outcome quite satisfactory. The evaluation with real data seems to be sufficient for the use in the awakening controller because the system is only based on discrete states of alertness.

Figure 12:
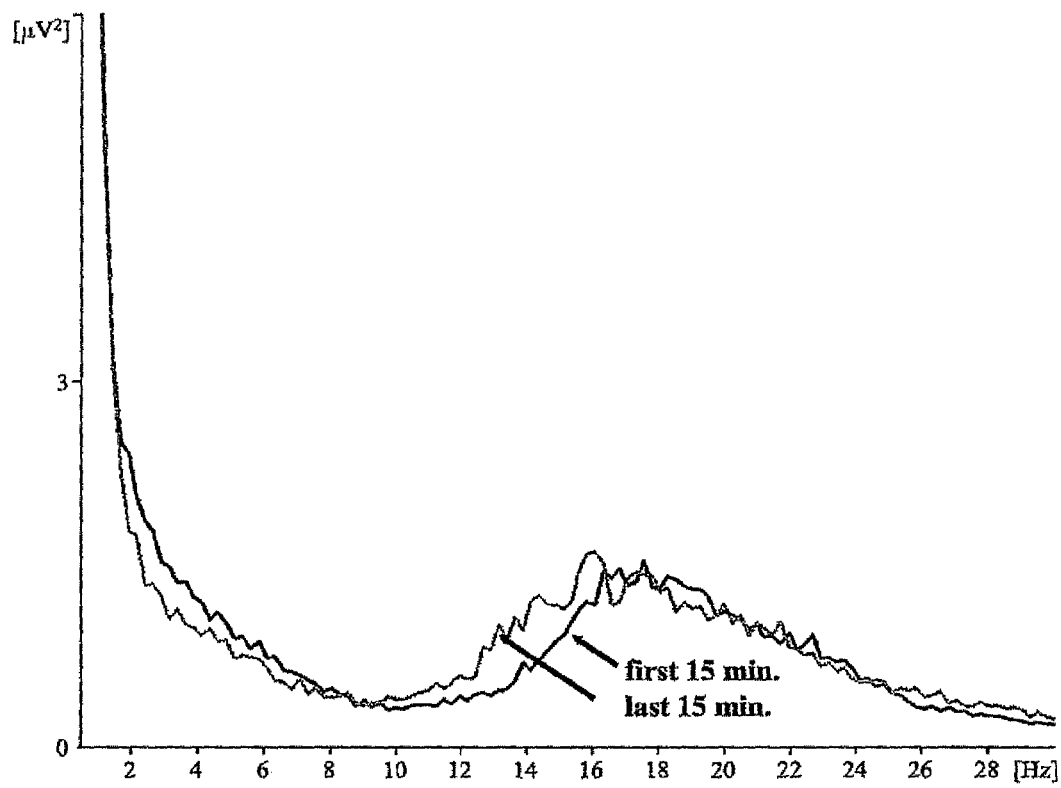
FIG. 12 shows an EEG frequency power spectrum during an intervention using a system according to the invention.

FIG. 12 shows an EEG frequency power spectrum during the intervention using a system according to FIG. 3. Additional to the cardiovascular relationship the changes in the EEG data can be verified and modelled. In FIG. 12 the distribution of the power spectrum vs. the frequency is shown. During a training (30 minutes) using a device as disclosed in WO00/61059 with a minimal conscious state patient the distribution of the power spectrum is changing. Comparing the power spectrum of the first 15 minutes to the last 15 minutes there is a shift of the distribution to lower frequencies (from the beta to the alpha frequency band).

This information (out of the EEG signal) is also used by the controller. The main difference to other signals like ECG is the time delay. The calculation of the distribution of the power spectrum will take a few minutes while the response of the heart rate can be analyzed after a few seconds. The controller always tries to minimize the error between the real data and the desired ones. For the heart rate this process will take place every 10 seconds whereas for the EEG-signals it will take place every 3 minutes. This enables the system to work in two different time frames. The controller is adapted to control with quick response times based on a first measurement signal acquired based on a fast physiological signal as well as take into consideration slow changes of a slow physiological signal. In this respect a fast physiological signal is a signal allowing response times of seconds to under one minute, preferably under 30 seconds, whereas a slow physiological signal is a signal necessitating response times of at least one, preferably two minutes.

Compared to an electric circuit, the interpreter computer unit 10 is the 'logic'-part of the whole concept. Here the different stages of the 'levels of awareness' $\vec{L}_a$ are determined.

Today, the state-of-the-art are clinical scores like Glasgow Coma Scale (GCS), Early Functional Abilities (EFA) and JFK Coma Recovery Scale-revised (JFC CRS-r). These three scores and other clinical scores are based on different functional assessment scales for auditory, visual, motor, communication and/or arousal behaviour. The general problem is the lack of a quantitative description for different levels of awareness. The clinical scores are a rough classification as well as only a qualitative way for the rating among patients.

On the one hand the interpreter computer unit and database 10 is based on the state-of-the-art or—in other words—the qualitative description of the patient's state of alertness/awareness. The experience and knowledge of the medical doctors about the behaviour of the patients as well as the knowledge represented in the literature form the basic fundament of the database. On the other hand all the acquired physiological data is used to get a supplemental quantitative description of the states of alertness. Hildebrandt et al reported in "Heart Rate Variability under Sensorial Stimulation as a Prognostic Parameter for the Functional Outcome of Severe Head Injury" in Akt Neurologie 2000; 27, 22-28; about the dependencies between the level of alertness and the heart rate variability, ECG in general and the EMG signals respectively. For this interpreter additional signals and interconnections are used.

One possible example to describe the processing of the brain in a quantitative way is the P300. The P300 is a neural evoked potential component of the electroencephalogram (EEG). This event-related potential appears as a positive deflection of the EEG voltage at approximately 300 ms and is supposed to follow unexpected auditory stimuli. Latency and amplitude of the P300 signal can be used as an indicator for the state of alertness. A short latency is equivalent for a fast brain processing and, thus, for a high level of alertness. Due to the distinct variability among the subjects normalized parameters are helpful. The area between the normal graph and the deflection one is used as one solution for that normalization issue.

Figure 13:
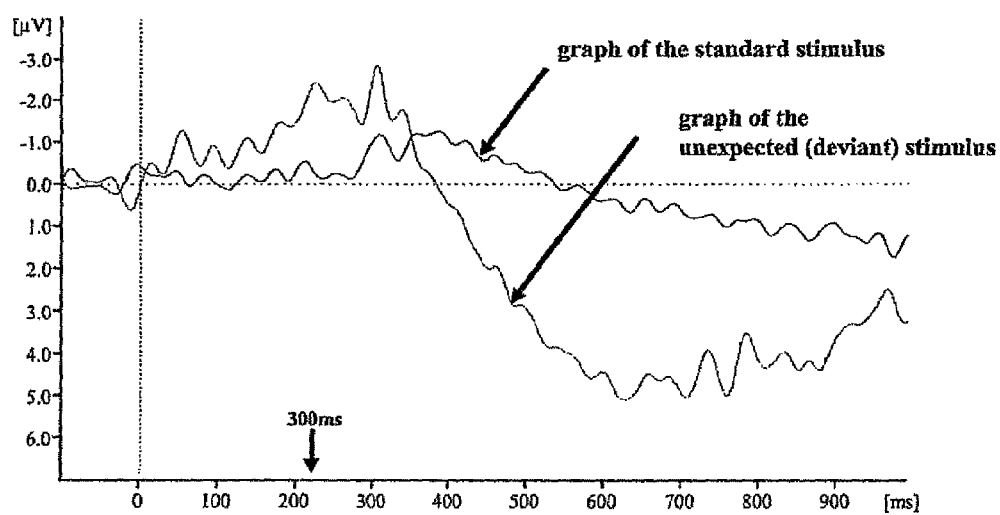
FIG. 13 shows two P300 graphs of a patient at the CPz-electrode of a 10-20 EEG system during an intervention using a system according to the invention.

FIG. 13 shows two P300 graphs of a patient at the CPz-electrode of a 10-20 EEG system. Additionally, from the artefact-compensated EEG data subparameters can be extracted such as frequency band ratios. All the subparameters are fitted together in a set of weighted parameters. This affirms the statement about the level of alertness as mentioned above.

Using a variety of different relationships, the interpreter unit 10 decides which choice of input signals may lead to different levels of alertness. Thus, the interpreter unit 10 chooses a special subset of input signals or parameters, which are probably 'good' for an individual patient in the sense that they lead to an output of the sensors relating to a higher level of alertness.

The advantage of the system according to the invention is the fact, that there is of course not only one optimal set of parameters for the vector of input parameters. There are a number of such subsets which all allow to reach. 'local maxima' in the resulting measured multi-dimensional vector signal, in the sense that each sensor contributes one scalar value to the vector signal or that a subset of sensors contributes a subset of scalar values to the resulting vector signal representing an awareness level. For example the combination of a higher heart rate with characteristic galvanic skin response and a drift of the distribution of the brain activity towards the alpha frequency band is an expression for a high level of alertness shown in a three-dimensional vector.

In a first control step the input for the awakening controller tries to reach exactly this set of parameters by using the appropriate stimuli via the vector $\vec{S}$ and the multi-modal display 50 respectively, as shown in the drawings relating to the embodiments in FIG. 1 to 8. If this strategy will not achieve a predefined satisfactory result, the set of parameters will be changed. In the next step the combination of a higher heart rate with characteristic galvanic skin response and a higher oxygen saturation should be reached. This second set of parameter stands also for a high level of alertness—the next 'local maximum'. All these stages and the corresponding sets of parameters as well as threshold of the decision relating to the choice of target vector $\vec{S}$ are part of the interpreter unit 10.

The signal vector displaying a higher 'state of alertness' can be composed from a subset of the following single signals:
- ECG: increasing of the LF/HF-ratio (LF: low frequency; HF: high frequency) and increasing of the heart rate variability may leads to an increase of the state of alertness
- EEG: decrease of the time delay and increase of the amplitude of late Event-Related Potentials (like P300), increase of the power within the frequency bands (theta, alpha) and a decreasing of the amount of 'slow wave activity' (delta frequency band: 0.25-4 Hz) will in the most cases lead to a higher state of alertness
- Respiration frequency: an increase of the frequency and an increase of the power within the high frequency bands (by means of a power spectrum analysis) may leads to an increase of the state of alertness
- EMG: patients with a higher state of alertness show an increase of muscle activity at the forehead
- Galvanic Skin Response (GSR): a rapid increase of the GSR signal may leads to an increase of the state of alertness The set of parameters of the interpreter computer unit 10 can use the direct correlation between some of the signals:
- increasing of the heart rate is correlated with a rapid increase of the galvanic skin response and/or increase of respiratory frequency and/or increase of $O_2$ saturation which can be a sign for a higher state of alertness
- increasing of event-related eye movements (events) correlated with an increase of respiratory frequency and/or increase of galvanic skin response and/or rapid increase of the heart rate variability can lead to a higher state of alertness
- event-related eye movement: an increase of directed eye movements correlated with events (e.g. external stimuli and also events in the room like 'walking/moving of the investigator') will in most cases lead to a higher state of alertness
- increasing of body temperature correlated with a decrease of 'slow wave activity' in the EEG power spectrum may lead to a higher state of alertness
- eye movement correlated with an increasing EEG power spectrum within the gamma band should lead to a higher state of alertness During the intervention, i.e. while taking signals of the sensors 20 i.e. during measurement:
- a global decreasing of galvanic skin response during the intervention can lead to a higher state of alertness
- changing of respiratory patterns: patients with a higher state of alertness show regular recurrent respiratory patterns
- patients with a higher state of alertness should show an increasing of $O_2$ saturation during the training.

An additional experiment was done with a healthy subject. The control strategy relates to an embodiment with the combination of the feedforward and feedback control as in FIG. 3, wherein only the heart rate (HR) will be controlled by means of the inverse model and a P controller. The chosen display is the inclination angle for a device as disclosed in WO00/61059.

First the individual range of the heart rate (HR) was determined. After laying 5 minutes in supine position, the inclination angle changes from 0° to 75°. For a baseline measurement the whole duration is 15 minutes and the stepping frequency has a constant value of 0.4 Hz. For this subject the averaged 'low' heart rate is 62.5 bpm (beats per minute) and the 'high' one is 76 bpm at an inclination angle of 0° and 75°, respectively. These values are necessary to obtain the maximal range of the HR (related to the tilting angle) as well as to identify the dynamic inverse model 40.

Figure 14:
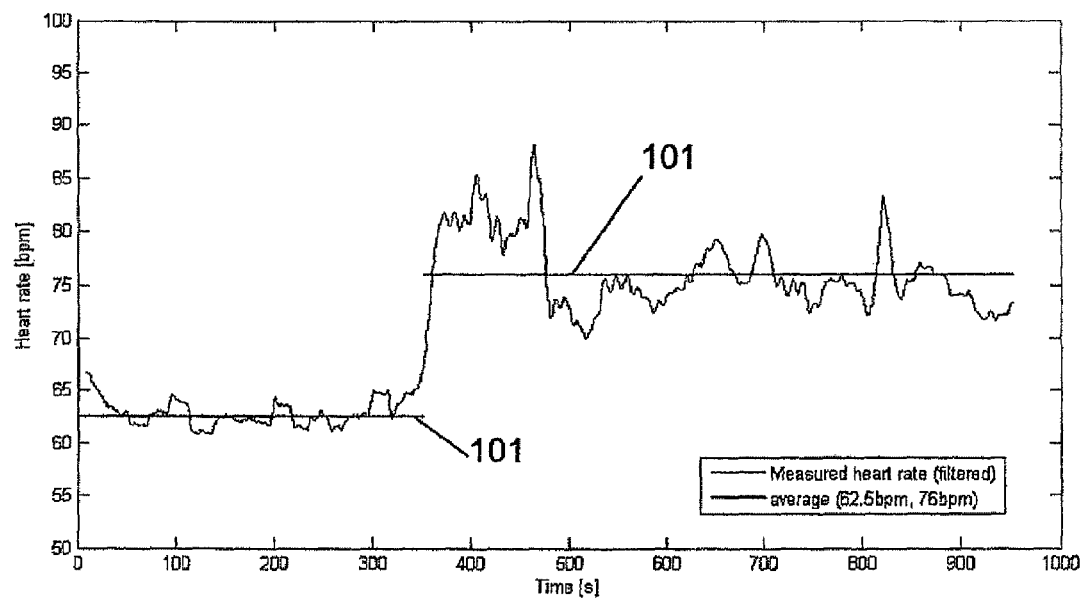
FIG. 14 shows that during an experiment, while the inclination angle as display value changes from 0° to 75°, the average heart rate as output signal changes from 62.5 to 76 bpm.

FIG. 14 shows that during the experiment, while the inclination angle changes from 0° to 75°, the average heart rate (shown as flat line 101) changes from 62.5 to 76 bpm; the stepping frequency is a constant value of 0.4 Hz during the whole experiment.

The investigator chooses a HR of 72 bpm (in the range of the low and high HR) as the desired one ($HR_d$). The desired value is the input of an inverse dynamic model describing the physiological process of the HR. The model determines the required angle $\alpha_m$ and as a result the device is tilting the subject to this angle. The recorded signal ($HR_{se}$) is acquired by means of ECG electrodes. In the feedback loop $HR_{se}$ is compared to the reference value $HR_d$ and the error fed into the P controller. The controller determines the required angle $\alpha_e$ and provokes a modification of the tilting angle $\alpha_{tilt}$.

Figure 15:
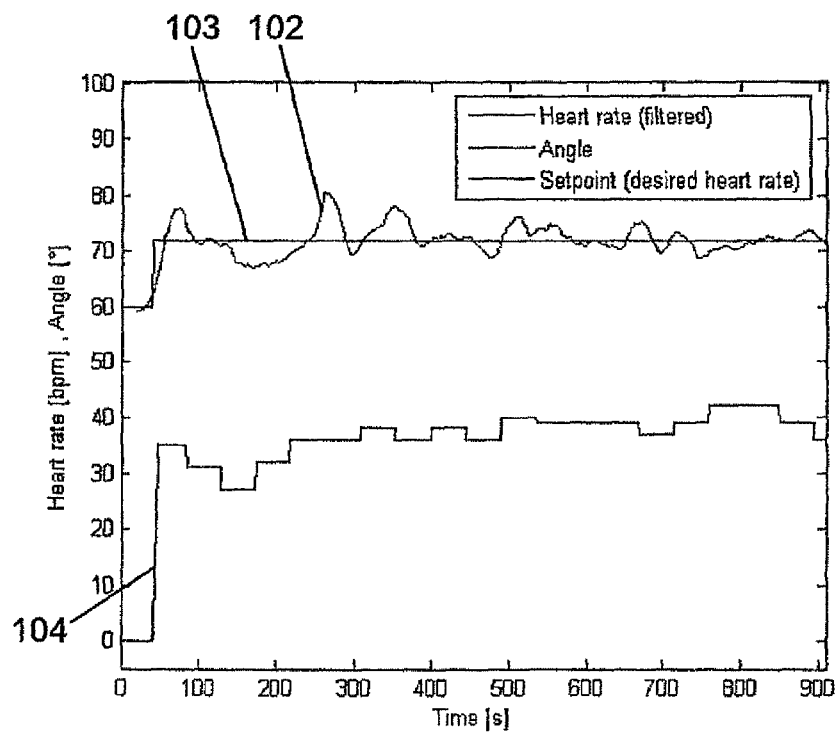
FIG. 15 shows the experiment with a desired heart rate of 72 bpm whereas the tilting angle $\alpha_{tilt}$ is modified by means of a P controller according to FIG. 3.

As shown in FIG. 15 the regulation of the HR (by means of the tilting angle) turns out satisfactory. While during the first minutes the over- und undershoots 102 are quite obvious, the actual HR swings into the desired value 103 in the second part of the experiment. Furthermore the angle $\alpha_e$ (which modifies the tilting angle $\alpha_{tilt}$) 104 decreases during the examination.

LIST OF REFERENCE SIGNS 10 interpreter computer unit
20 sensor
21 additional input
22 adaptation extension input path
23 adaptive part path
24 additional adaptive extension input
25 path
26 path
30 patient
40 inverse model
41 awakening controller
42 controller
50 display
60 safety-monitoring unit
70 direct model
80 adaptation mechanism
91 pulse transit time
92 inverted pulse transit time
101 heart rate (shown as flat line)
102 over- und undershoots of heart rate
103 desired value of heart rate
104 angle of inclination

The invention claimed is:

1. A rehabilitation system for neurological disorders comprising:
   at least two sensors measuring different physiological values of a patient;
   a memory storing parameters unique to the patient and an injury;
   at least two stimulation generators; and
   a computer processor,
   wherein the memory is connected to the computer processor such that said parameters are delivered from the memory to the computer processor, and the at least two sensors are connected to the computer processor such that measurement signals are delivered from the at least two sensors to the computer processor, further wherein the computer processor:
   initially generates predefined target signals determined and based on the parameters;

during a rehabilitation session, compares the measurement signals with the target signals and drives the at least two stimulation generators delivering sensory stimulation to the patient as feedback; and the computer processor changes the predefined target signals during the rehabilitation session based on development or changes of the measurement signals of the different physiological values, further wherein the target signals are arranged as a target vector signal, the at least two measurement signals are arranged as a measured vector signal, and the measured vector signal is compared with the target vector signal to obtain a comparison result which controls and drives the at least two stimulation generators delivering different sensory stimulation to the patient as feedback, and a time interval and an improvement threshold vector are defined for a rehabilitation session, wherein at an end of such a time interval, a change of initial measurement signals to current measurement signals and/or a difference of current measurement signals with existing target signals is compared to the improvement threshold vector and, if an improvement does not reach the improvement threshold vector, the at least two stimulation generators delivering sensory stimulation to the patient as feedback are set to follow new predefined target signals.

2. The system according to claim 1, wherein the at least two sensors are selected to acquire measurement signals of physiological values within different time frames.

3. The system according to claim 2, further comprising different closed-loop controllers provided for each signal within a different time frame.

4. The system according to claim 3, wherein the different closed-loop controllers are provided for each signal within a different time frame.

5. The system according to claim 4, wherein one controller of the different closed-loop controllers is adapted to use a time frame larger than one minute, and another controller of the different closed-loop controllers is adapted to use a time frame shorter than one minute.

6. The system according to claim 3, wherein one sensor acquires the heart rate of a patient and one other sensor is adapted to acquire an EEG signal.

7. The system according to claim 1, wherein the comparison result of the vector signals is mapped through use of a control array onto a control vector signal to drive the at least two stimulation generators.

8. The system according to claim 1, wherein the at least two stimulation generators are chosen from the group encompassing a leg or arm movement generator, a tilting board/bench for body verticalization, a graphical display, an acoustic display, a tactile stimulator or vibrator, an olfactory display, a source of heat, a source of cold, or any combination thereof.

9. A rehabilitation system for neurological disorders comprising:

at least two sensors measuring two different physiological values of a patient;

a memory storing parameters unique to the patient and an injury;

at least two stimulation generators; and a computer processor, wherein the memory is connected to the computer processor, such that the parameters from the memory are delivered to the computer processor and the at least two sensors are connected to the computer processor such that measurement signals from the at least two sensors are delivered to the computer processor, wherein the computer processor:

initially generates predefined target signals determined and based on the parameters; and during a rehabilitation session, compares the measurement signals with the target signals and drives the at least two stimulation generators delivering sensory stimulation to the patient as feedback, wherein the target signals are arranged as a target vector signal, the at least two measurement signals are arranged as a measured vector signal, and the measured vector signal is compared with the target vector signal to obtain a comparison result which controls and drives the at least two stimulation generators delivering different sensory stimulation to the patient as feedback, wherein the comparison result of the vector signals is mapped through use of a control array onto a control vector signal to drive the at least two stimulation generators, and a time interval and an improvement threshold vector are defined for a rehabilitation session, wherein at an end of such a time interval, a change of initial measurement signals to current measurement signals and/or a difference of current measurement signals with existing target signals is compared to the improvement threshold vector and, if an improvement does not reach the improvement threshold vector, the at least two stimulation generators delivering sensory stimulation to the patient as feedback are set to follow new predefined target signals.

10. The system according to claim 9, wherein the at least two stimulation generators are chosen from the group encompassing a leg or arm movement generator, a tilting board/bench for body verticalization, a graphical display, an acoustic display, a tactile stimulator or vibrator, an olfactory display, a source of heat, a source of cold, or any combination thereof.

11. The system according to claim 9, wherein the sensors are chosen from the group defining physiological quantities encompassing EEG signals and Evoked Potentials, EMG signals, heart rate, systolic and diastolic blood pressure, respiration frequency, skin conductance, oxygen saturation, body temperature, or any combination thereof.

* * * * *